(12) United States Patent
Liu et al.

(10) Patent No.: US 10,792,008 B2
(45) Date of Patent: Oct. 6, 2020

(54) PREPARATION METHOD OF RADIOACTIVE SOURCE

(71) Applicant: Shanghai Neusoft Medical Technology Co., Ltd., Shanghai (CN)

(72) Inventors: Yue Liu, Shenyang (CN); Zhipeng Sun, Shenyang (CN); Ming Li, Shenyang (CN)

(73) Assignee: SHANGHAI NEUSOFT MEDICAL TECHNOLOGY CO., LTD., Shanghai (CN)

( * ) Notice: Subject to any disclaimer, the term of this patent is extended or adjusted under 35 U.S.C. 154(b) by 0 days.

(21) Appl. No.: 16/049,626

(22) Filed: Jul. 30, 2018

(65) Prior Publication Data

US 2019/0029631 A1    Jan. 31, 2019

(30) Foreign Application Priority Data

Jul. 31, 2017    (CN) .......................... 2017 1 0642119

(51) Int. Cl.
| | |
|---|---|
| *A61B 6/00* | (2006.01) |
| *A61B 6/03* | (2006.01) |
| *G01T 1/29* | (2006.01) |
| *G01T 7/00* | (2006.01) |

(52) U.S. Cl.
CPC .............. *A61B 6/58* (2013.01); *A61B 6/037* (2013.01); *A61B 6/583* (2013.01); *A61B 6/585* (2013.01); *G01T 1/2985* (2013.01); *G01T 7/005* (2013.01)

(58) Field of Classification Search
CPC ....................................................... A61B 6/58
See application file for complete search history.

(56) References Cited

U.S. PATENT DOCUMENTS

| | | | | |
|---|---|---|---|---|
| 7,682,540 | B2 * | 3/2010 | Boyan ..................... | A61L 27/16 264/212 |
| 8,796,637 | B1 | 8/2014 | Burr et al. | |
| 2004/0253294 | A1 * | 12/2004 | Tabata ................. | A61K 9/0019 424/426 |
| 2017/0209606 | A1 * | 7/2017 | Azab ...................... | A61K 51/06 |

FOREIGN PATENT DOCUMENTS

| | | |
|---|---|---|
| CN | 101111781 A | 1/2008 |
| CN | 101593567 A | 12/2009 |
| CN | 101777399 A | 7/2010 |
| CN | 102647945 A | 8/2012 |
| CN | 104412127 A | 3/2015 |
| CN | 104720839 A | 6/2015 |
| CN | 104799879 A | 7/2015 |
| CN | 106296768 A | 1/2017 |

OTHER PUBLICATIONS

State Intellectual Property Office of the People's Republic of China, Office Action and Search Report Issued in Application No. 201710642119.2, dated Feb. 27, 2020, 18 pages. (Submitted with Machine Translation).

* cited by examiner

*Primary Examiner* — Michael G. Hartley
*Assistant Examiner* — Jagadishwar R Samala
(74) *Attorney, Agent, or Firm* — McCoy Russell LLP

(57) ABSTRACT

A radioactive source and preparing as well as applying methods are disclosed. According to the method of preparing the radioactive source, when a preset dose of a radiopharmaceutical with a half-life shorter than a preset threshold is provided, a solid radioactive source having a predetermined shape may be obtained by mixing and moulding the radiopharmaceutical with a preset solution and a moulding material. The moulding material may comprise a curing agent and/or a water-absorbing material.

2 Claims, 5 Drawing Sheets

PREPARATION METHOD OF RADIOACTIVE SOURCE

CROSS REFERENCE TO RELATED APPLICATIONS

This application claims priority to Chinese Patent Application No. 201710642119.2 filed on Jul. 31, 2017, the entire contents of which is hereby incorporated by reference in its entirety for all purposes.

BACKGROUND

A radioactive source is prepared from a radiopharmaceutical. Data collected from a radioactive source can be used to perform state detection, system calibration, and correction factors generation for nuclear medicine apparatuses. For example, Positron Emission Tomography (PET) device needs to use a radioactive source for quality inspection before leaving a factory. In addition, in daily use, a radioactive source is also required for periodic quality inspection.

NEUSOFT MEDICAL SYSTEMS CO., LTD. (NMS), founded in 1998 with its world headquarters in China, is a leading supplier of medical equipment, medical Information Technology (IT) solutions, and healthcare services. NMS supplies medical equipment with a wide portfolio, including Computed Tomography (CT), Magnetic Resonance Imaging (MM), digital X-ray machines, ultrasound, Positron Emission Tomography (PET), Linear Accelerator (LINAC), and biochemistry analysers. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

DETAILED DESCRIPTION

The following describes the specific contents of the present disclosure.

At present, medical apparatuses (such as PET device) generally use liquid radioactive sources. However, due to the fluidity of the liquid radioactive source, the operation of the apparatuses is complicated and the control of the apparatuses is difficult.

Figure 1:
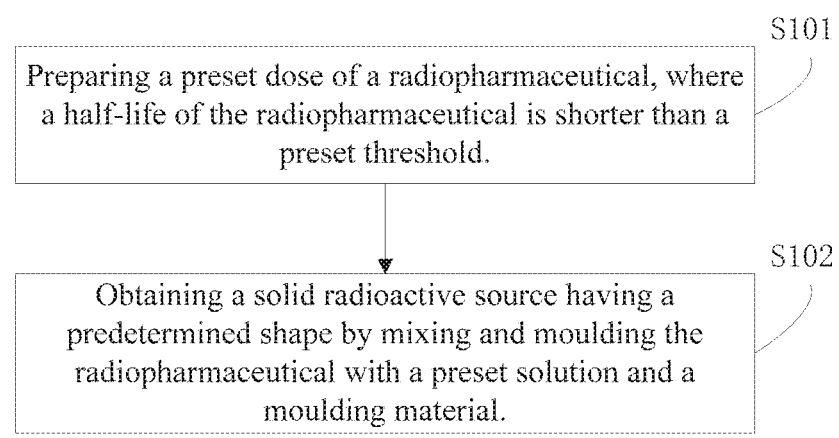
FIG. 1 is a flowchart illustrating a processing of a method of preparing a radioactive source according to an example of the present disclosure.

For this reason, an example of the present disclosure provides a method of preparing a radioactive source. As shown in FIG. 1, a processing of a method of preparing a radioactive source according to an example of the present disclosure is illustrated. The method of preparing a radioactive source specifically includes:

At step S101, a preset dose of a radiopharmaceutical whose half-life is shorter than a preset threshold is prepared.

Radioactive sources using longer half-life radiopharmaceuticals are high cost and have strict radiation protection requirements for a storage space. Therefore, the examples of the present disclosure restrict the selection of radiopharmaceuticals, that is, use a radiopharmaceutical with a half-life shorter than a preset threshold. Usually a radiopharmaceutical with a half-life shorter than 7 days is selected, for example, Fludeoxyglucose F 18 ($^{18}$F-FDG).

At step S102, a solid radioactive source having a predetermined shape is obtained by mixing and moulding the radiopharmaceutical with a preset solution and a moulding material.

The preset solution in the examples of the present disclosure may be water or other solutions that do not react with the radiopharmaceutical, for example, a sodium chloride solution.

An example of the present disclosure may include preparing a curing agent as the moulding material, mixing the radiopharmaceutical with the solution and the curing agent to obtain a first mixture, and placing the first mixture into a mould with a predetermined shape to obtain the solid radioactive source.

Specially, in one implementation, when the moulding material is a curing agent, the preset solution and the curing agent may be first prepared within a ratio range. For example, when the preset solution is 100 ml, and if gelatin is used as the curing agent, the dose of gelatin may be 10 g-15 g. Next, the radiopharmaceutical, the preset solution, and the curing agent are thoroughly mixed to obtain a first mixture. Again, the first mixture is placed into a mould of a predetermined shape. After a period of time, a solid radioactive source with the predetermined shape is obtained. Among them, the curing agent may include gelatin, gypsum powder, and the like.

Another example of the present disclosure may include mixing the radiopharmaceutical with the solution to obtain a second mixture, preparing a water-absorbing material as the moulding material, moulding the water-absorbing material into a predetermined shape; and placing the water-absorbent material with the predetermined shape into the second mixture to obtain the solid radioactive source.

In another implementation, when the moulding material is a water-absorbing material, the radiopharmaceutical is first uniformly mixed with the preset solution to obtain a second mixture. Then a water-absorbing material having a preset ratio range to the second mixture is prepared. For example, in one implementation, the water-absorbing material is a hydrogel, and the preset ratio range of the second mixture to the hydrogel may be (150 to 2000):1. Again, the water-absorbing material is moulded into a predetermined shape. Finally, the water-absorbing material is placed into the second mixture and the absorption of the water-absorbing material is waited until a solid radioactive source with the predetermined shape is obtained. Among them, the water-absorbing material may include a hydrogel, a phenolic plastic, a super absorbent polymer, and the like.

It may be understood that the concentration of the radiopharmaceutical is determined by the specific application scenario. In addition, the preset ratio range is different when the selected moulding material is different.

In the method for preparing a radioactive source provided in the examples of the present disclosure, firstly a preset dose of a radiopharmaceutical is obtained whose half-life is shorter than a preset threshold. Then, the radiopharmaceutical with a preset solution and a moulding material are mixed and moulded to obtain a solid radioactive source having a predetermined shape. A solid radioactive source provided by the examples of the present disclosure has a relatively low cost and is moulded to a shape that meets the needs of users. The inconvenience caused by the fluidity of a liquid radioactive source may be avoided by employing the described example methods.

Hereinafter, the preparation methods of the radioactive source provided by examples of the present disclosure will be described by taking several specific operations of radioactive source preparations as examples.

In a specific radioactive source preparation method, firstly a preset dose of $^{18}$F-FDG and water are thoroughly mixed to obtain 100 ml of an aqueous solution. For example, 0.1 mCi of $^{18}$F-FDG may be added to 100 ml of water. Then, 10 g-15 g of gelatin is added to the aqueous solution to obtain a first mixture. Next, the first mixture is heated to a temperature of approximately 35° C. to 105° C. until the gelatin completely dissolves. Then the first mixture is left to stand at a temperature of −20° C. to 20° C. When the first mixture is solidified into a semi-colloid, the first mixture is put into a predetermined mould to be moulded. The first mixture may be left standing until the first mixture is completely solidified, and the solid radioactive source with the predetermined shape is obtained.

In addition, the first mixture in which the gelatin is completely dissolved may be directly poured into the predetermined mould and stood in a temperature range of −20° C. to 20° C. until the first mixture is solidified into the solid radioactive source.

In addition, in order to speed up the solidification of the first mixture, in an example of the present disclosure, after pouring the first mixture in which the gelatin is completely dissolved into a predetermined mould, the first mixture may be stood in a temperature lower than −20° C. to accelerate the solidification.

In another specific radioactive source preparation method, under a normal air pressure condition, $^{18}$F-FDG and water are mixed thoroughly to obtain a aqueous solution, and temperature is controlled among 0° C. to 35° C. An appropriate amount of gypsum powder having fineness above 170 meshes is added and thoroughly stirred, and the first mixture is obtained. For example, gypsum powder having a fineness of 300 meshes is added to the aqueous solution. When using gypsum powder, the ratio of the aqueous solution to the gypsum powder is approximately 1:0.27. The first mixture is poured into a predetermined mould and stood for a period of time, and the solid radioactive source with a predetermined shape is obtained after the first mixture is finally solidified.

The radiopharmaceutical may be firstly added to the preset solution with thorough mixing, and then the curing agent may be added. Alternatively, the curing agent and the preset solution may be mixed first, and then the radiopharmaceutical may be added with thorough mixing before solidified. The present disclosure does not limit the mixing order of the radiopharmaceutical, the preset solution, and the curing agent.

In another specific radioactive source preparation method, $^{18}$F-FDG and water are thoroughly mixed under normal temperature and pressure conditions to obtain a second mixture, and then an appropriate amount of a hydrogel, such as a spherical hydrogel, with a predetermined shape is added. The specific ratio of the second mixture to the spherical hydrogel should meet the preset ratio range of (150 to 2000):1. After waiting for the spherical hydrogel to fully absorb the second mixture to achieve absorption equilibrium, the solid radioactive source having the predetermined shape is obtained.

It is worth noting that the hydrogel may also be replaced with other hydrophilic polymer materials which are insoluble in water.

To sum up, with the above methods, the examples of the present disclosure may produce a solid radioactive source that meets the user's needs, and a convenient user operation and control may be achieved.

The method for preparing a radioactive source according to an example of the present disclosure can be applied to diagnose nuclear medicine apparatuses such as PET, PET/MR, PET/CT, and Single-Photon Emission Computed Tomography (SPECT). The following are examples of applications of the radioactive source to a PET device, such as quality inspection of a device, correction factor generation, and device calibration.

Figure 2:
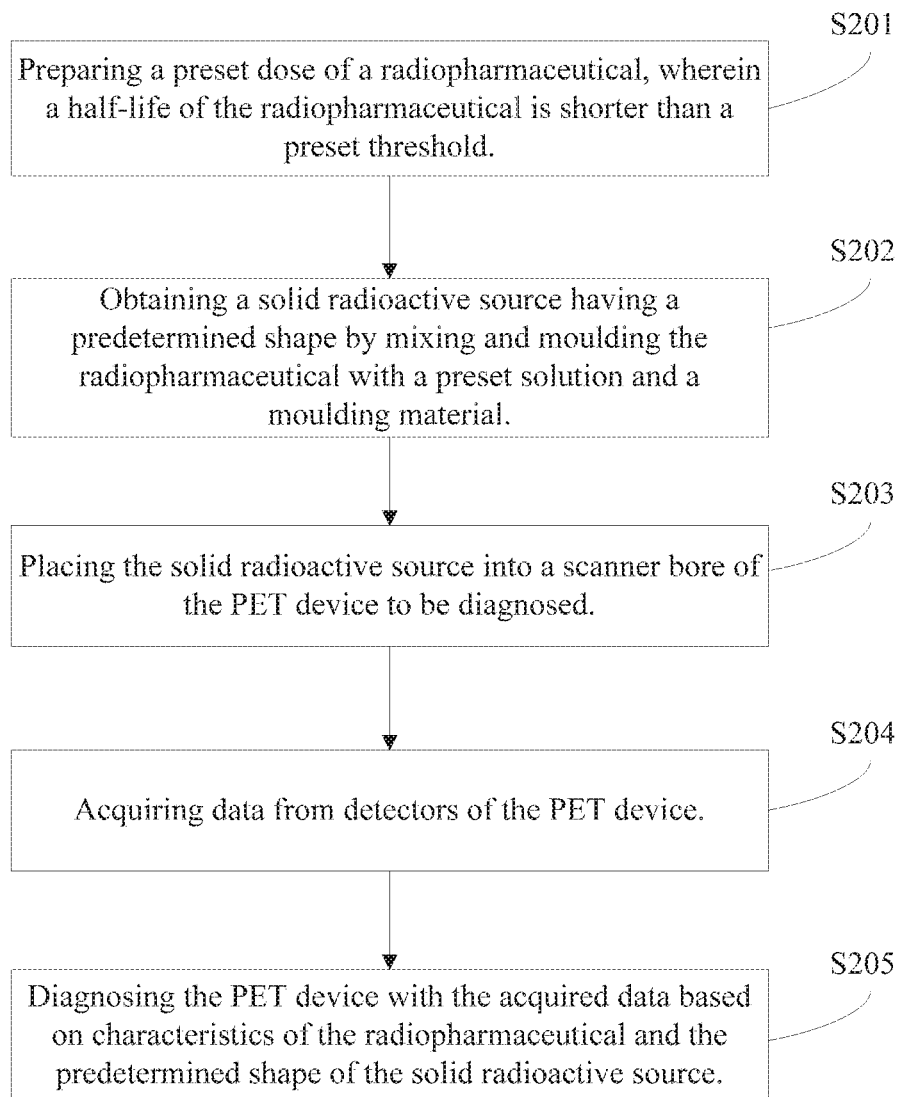
FIG. 2 is a flowchart illustrating a processing of a method of diagnosing a PET device according to an example of the present disclosure.

An example of the present disclosure provides a method of diagnosing a PET device. Shown in FIG. 2 is a flowchart illustrating a processing of a method of diagnosing a PET device according to an example of the present disclosure. The PET diagnosing method specifically includes:

At step S201, a preset dose of a radiopharmaceutical whose half-life is shorter than a preset threshold is prepared.

At step S202, a solid radioactive source having a predetermined shape is obtained by mixing and moulding the radiopharmaceutical with a preset solution and a moulding material.

The implementation processes of the above steps S201-S202 are understood with reference to the steps S101-S102, and will not be described here.

The shape of the radiation source may be determined according to the specific requirements of the PET device to be diagnosed.

At step S203, the solid radioactive source is placed into a scanner bore of the PET device to be diagnosed.

At step S204, data from detectors of the PET device are acquired.

At step S205, a diagnosing result of the PET device is determined according to the acquired data based on characteristics of the radiopharmaceutical and the predetermined shape of the solid radioactive source.

The characteristics of the radiopharmaceutical may include the half-life of the radiopharmaceutical, the concentration of the radiopharmaceutical, and the like.

Diagnosing a PET device may include quality inspection of the PET device, correction factor generation of the PET device, and PET calibration. For different diagnosing purposes, the corresponding processing methods of emitted data from the radiation source are also different. The following are more detailed descriptions based on various application scenarios.

Figure 3:
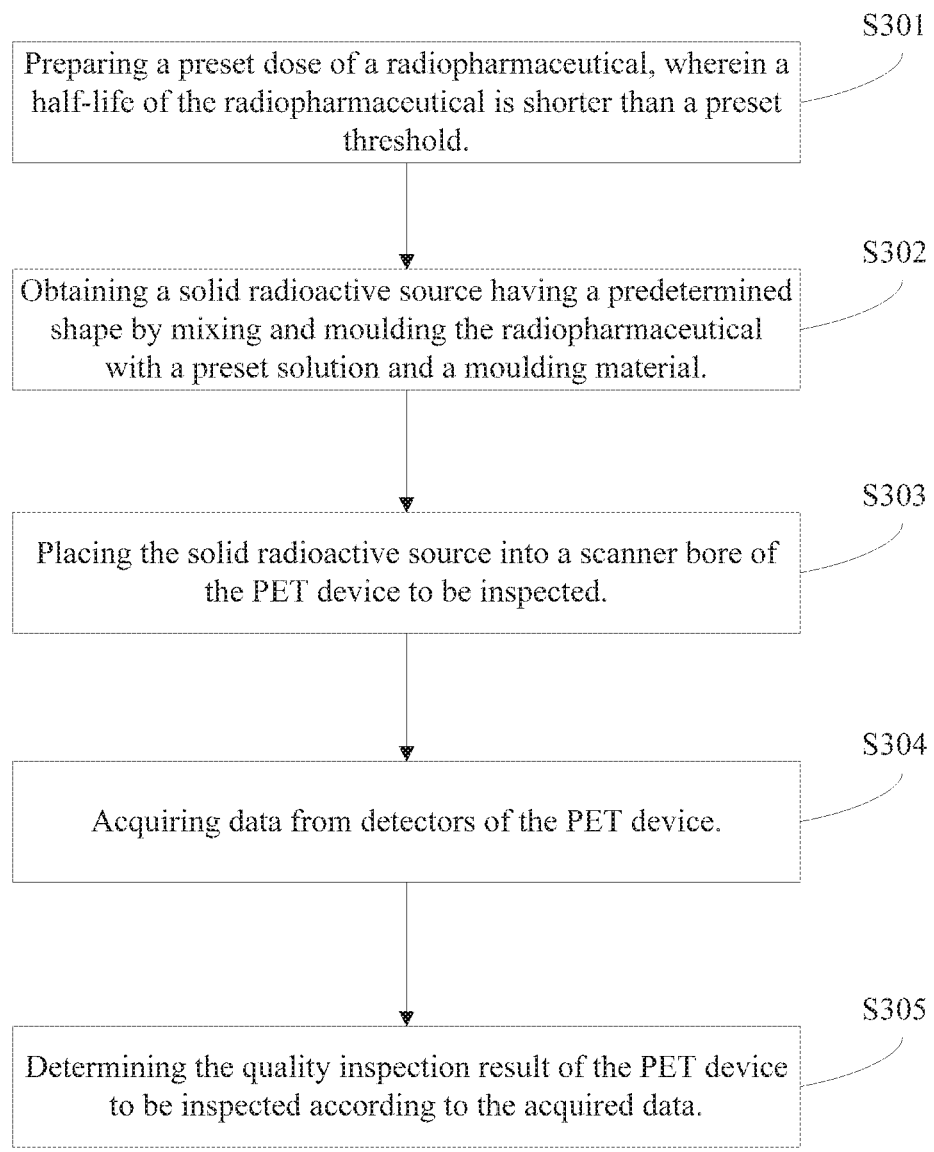
FIG. 3 is a flowchart illustrating a processing of a method of quality inspecting for a PET device according to an example of the present disclosure.

FIG. 3 is a flowchart illustrating a processing of a method of quality inspecting for a PET device according to an example of the present disclosure. The quality inspection method of the PET device specifically includes:

At step S301, a preset dose of a radiopharmaceutical whose half-life is shorter than a preset threshold is prepared.

At step S302, a solid radioactive source having a predetermined shape is obtained by mixing and moulding the radiopharmaceutical with a preset solution and a moulding material.

The implementation processes of the above steps S301-S302 are understood with reference to the steps S101-S102, and will not be repeated here.

In addition, since a cylindrical type radioactive source is generally used for quality inspection of a PET device, in this example, when a radioactive source is prepared, the radioactive source is moulded into a cylindrical shape as the radioactive source for the quality inspection. Specifically, the mixture is poured into the cavity of the cylindrical mould to form a cylindrical body and the cylindrical radioactive source is obtained.

At step S303, the solid radioactive source is placed into a scanner bore of the PET device to be inspected.

At step S304, data from detectors of the PET device are acquired.

At step S305, the quality inspection result of the PET device to be inspected is determined according to the acquired data.

In practical applications, prior to the quality inspection of the PET device, the prepared radioactive source is first placed into the PET device to be inspected. Detectors of the PET device collect photon rays emitted by the radioactive source and convert them into scan data which represent characteristics of the photons. The data may include parameters such as energy, location, and time. Since the data can reflect the status of the PET detectors, in the example of the present disclosure, the quality inspection result of the PET device can be determined by using the acquired data.

Specifically, after the data is obtained, the data is stored in a format of a chordal graph. If there are obvious dark stripes in the chordal graph, it indicates that the PET device to be inspected has an issue and fails the quality inspection.

In a practical application scenario, prior to the quality inspection of a PET device, a cylindrical radioactive source is prepared on site using a radiopharmaceutical whose half-life shorter than a preset threshold, and then the radioactive source is directly used for the quality inspection of the PET device. In this way, the storage issue of a solid radiation source with long half-life can be avoided.

In the quality inspection method of a PET device according to the example of the present disclosure, the PET device is inspected using a solid radioactive source prepared in advance. Compared with the quality inspection method using a liquid radiation source, this example avoids the problems of complicated operation and difficult control.

Figure 4:
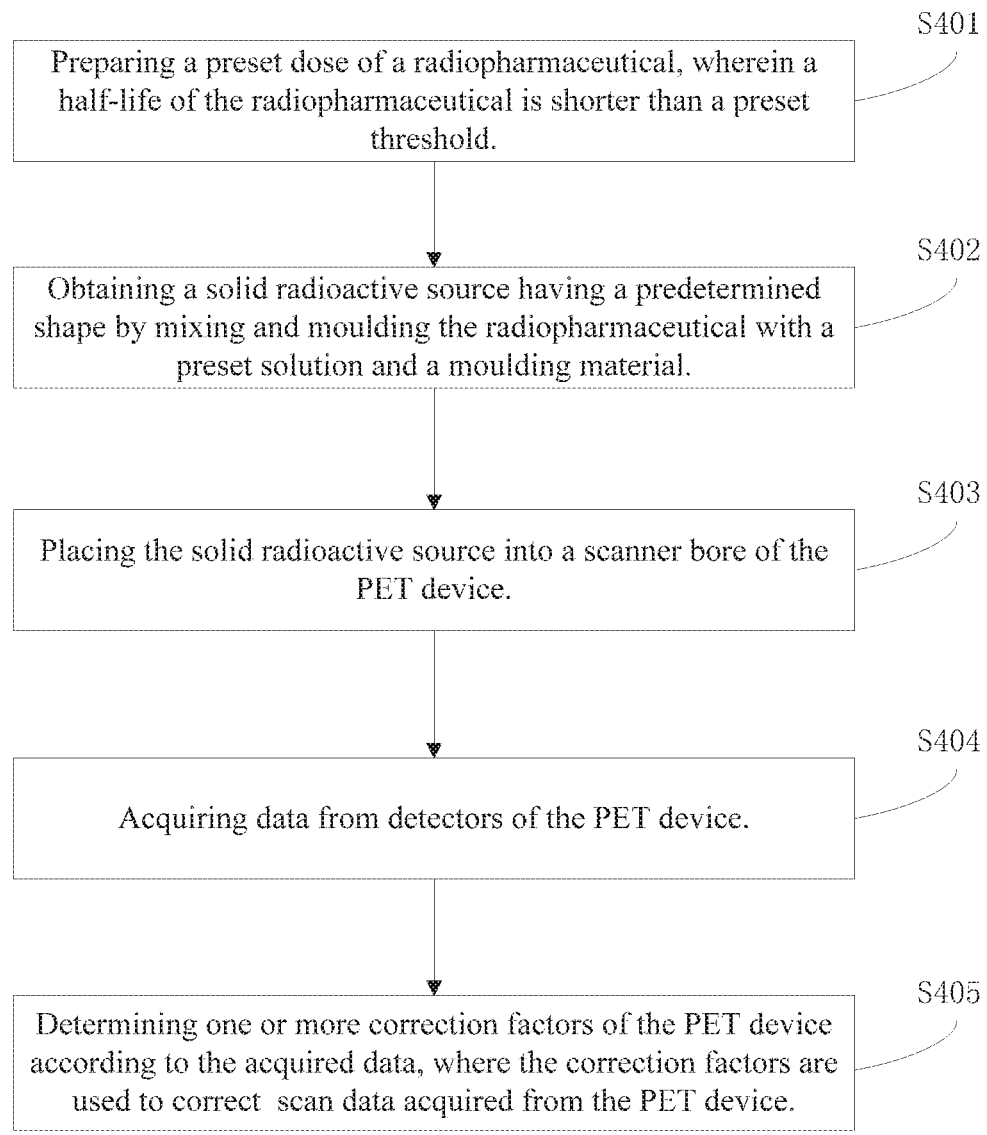
FIG. 4 is a flowchart illustrating a processing of a method of determining one or more correction factors for a PET device according to an example of the present disclosure.

In addition, an example of the present disclosure also provides a method for determining one or more correction factors of scan data of a PET device. Referring to FIG. 4, it is a flowchart illustrating a processing of a method of determining one or more correction factors for a PET device according to an example of the present disclosure. The method for determining the correction factor specifically includes:

At step S401, a preset dose of a radiopharmaceutical whose half-life is shorter than a preset threshold is prepared.

At step S402, a solid radioactive source having a predetermined shape is obtained by mixing and moulding the radiopharmaceutical with a preset solution and a moulding material.

The implementation processes of the above steps S401-S402 are understood with reference to the steps S101-S102, and will not be described here.

In the example of the present disclosure, when a radioactive source is prepared, the radioactive source is moulded into a cylindrical shape as the radioactive source for generating one or more correction factors of a PET device. Specifically, the mixture is poured into the cavity of the cylindrical mould to form a cylindrical body and the cylindrical radioactive source is obtained.

At step S403, the solid radioactive source is placed into a scanner bore of the PET device.

Specifically, when using the radioactive source to determine the correction factors of a PET device, the radioactive source is placed into the center of the field of view (FOV) of the PET device. The length of the radioactive source may extend the entire axial FOV of the PET device.

At step S404, data from detectors of the PET device are acquired.

At step S405, one or more correction factors of the PET device is determined according to the acquired data, where the correction factors are used to correct the scan data of the PET device.

In practical applications, after a PET device collects scan data which is emitted from a patient, the scan data need to be corrected in order to reconstruct a more accurate PET image. The general method is to correct the scan data by using one or more correction factors. Specifically, the correction factors may include a normalization correction factor and the like. The method for determining the PET correction factors provided by the example of the present disclosure includes using a solid radiation source prepared in advance to replace photon rays emitted by the patient. The radioactive source can be set, for example, to set the concentration of the radiopharmaceutical, to emit photons that meet the calculation requirements, and then the calculation algorithm may be used to calculate the normalization correction factor. Calculating the normalization correction factor according to the calculation formula of the correction factor may use common algorithms in the industry, such as Component-Based Normalization algorithm, and will not be described in detail here.

In the method for determining one or more correction factors of a PET device according to the example of the present disclosure, the correction factors of the PET device are determined by using a solid radioactive source prepared in advance. Compared with the determination method using a liquid radioactive source, this method avoids the problems of complicated operation and difficult control.

Figure 5:
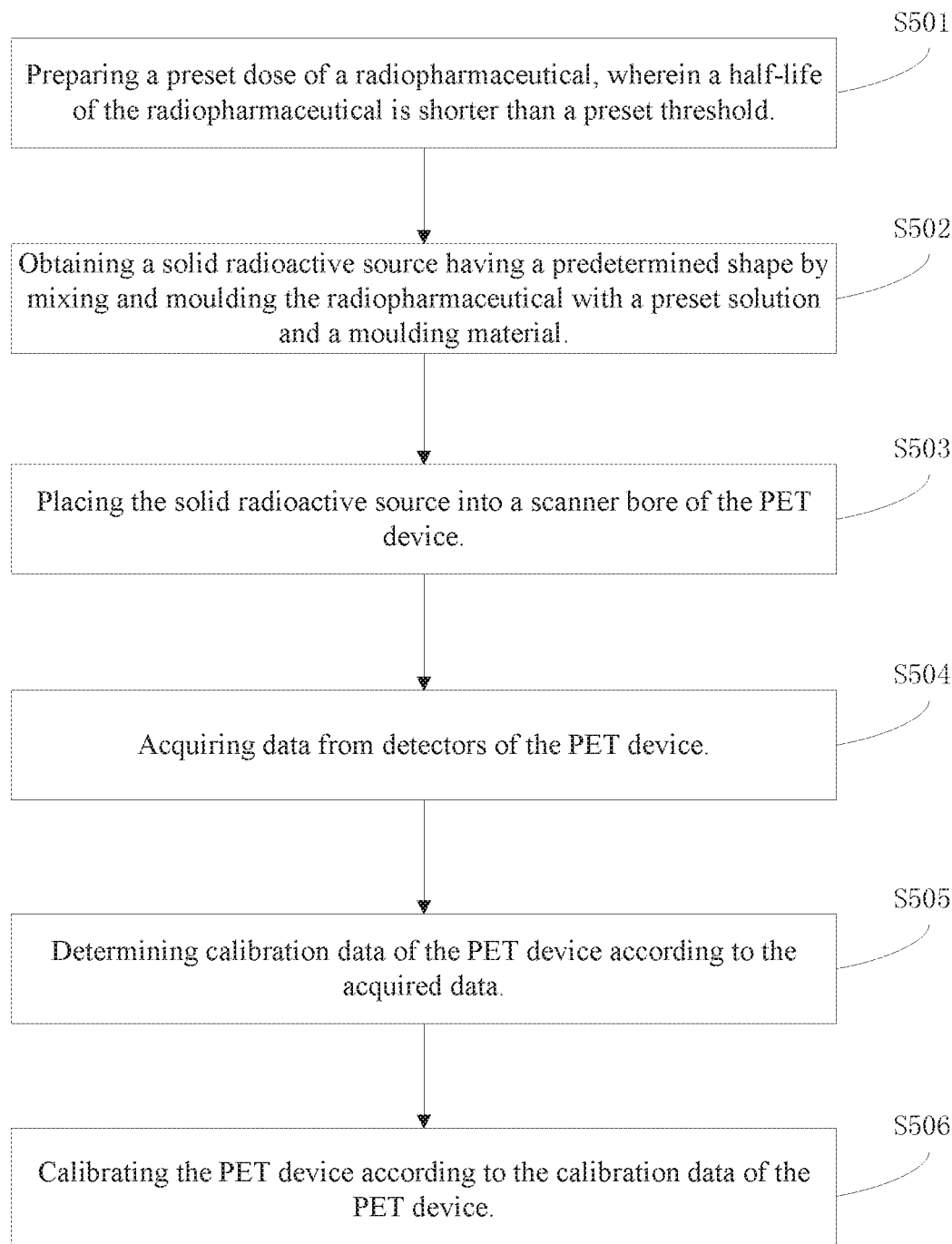
FIG. 5 is a flowchart illustrating a processing of a method of calibrating a PET device according to an example of the present disclosure.

In addition, an example of the present disclosure also provides a method for calibrating a PET device, which is specifically a method of calibrating the time alignment value of the PET device. Referring to FIG. 5, a flowchart is shown, illustrating a processing of a method of calibrating a PET device according to an example of the present disclosure. The PET calibration method specifically includes:

At step S501, a preset dose of a radiopharmaceutical whose half-life is shorter than a preset threshold is prepared.

At step S502, a solid radioactive source having a predetermined shape is obtained by mixing and moulding the radiopharmaceutical with a preset solution and a moulding material.

The implementation processes of the above steps S501-S502 are understood with reference to the steps S101-S102, and will not be repeated here.

In the example of the present disclosure, when a radioactive source is prepared, the radioactive source may be moulded into a cylindrical shape as the radioactive source for PET calibration. Specifically, the mixture is poured into the cavity of the cylindrical mould to form a cylindrical body and the cylindrical radioactive source is obtained.

At step S503, the solid radioactive source is placed into a scanner bore of the PET device.

Specifically, the radioactive source is placed into the center of the FOV of the PET device. The length of the radioactive source may extend the entire axial FOV of the PET device.

In addition, before using the radioactive source for the PET calibration, the time alignment value of the PET device may be set to zero.

At step S504, data from detectors of the PET device is acquired.

Specifically, the acquired data is stored in a listmode form, where the listmode form may completely store energy, position, time, and other information of each data.

In practical applications, for one detector crystal in any detector ring of a PET device, there is another detector crystal opposite to this detector crystal may near-simultaneously capture a pair of annihilation photons. Thereby one detector crystal pair is formed, and this capture may be called a coincidence event. For a detector crystal, there may be N detector crystal pairs. The line connecting the pair of two detector crystals is called the line of response (LOR). Each detector crystal may have N LORs. Each LOR of every detector crystal passes through the radioactive source. The detectors acquire the photon rays emitted by the radiation source, count the time differences between two detectors of a detector crystal pair receiving coincidence events, and form a histogram of the time differences.

At step S505, a calibration data of the PET device is determined according to the acquired data.

In practical applications, by the histogram storing the time differences in the PET device, the value corresponding to the time difference that has the largest amount can be determined. This value is used as the calibration data of the PET device. For example, if the largest amount corresponds to a time difference of 0.5 ns, this indicates that a 0.5 ns alignment error is present for coincidence events of the PET device. Accordingly, 0.5 ns is used as the time calibration data of the PET device.

At step S506, the PET device is calibrated according to the calibration data of the PET device.

In practical applications, after determining the calibration data of the PET device, the time alignment value of each detector in the PET device is updated by the calibration data. The updated time alignment value is used to align the coincidence events' timing for each detector crystal in the PET device.

In the PET calibration method according to the example of the present disclosure, a PET device is calibrated by using a solid radioactive source prepared in advance. Compared with the method of using a liquid radioactive source, this example avoids the problems of complicated operation and difficult control.

It could be understood that the above are only a few of common usages of a solid radioactive sources prepared by the present disclosure. Usages of the solid radioactive source prepared by the present disclosure are not limited to these several application methods. Applications of liquid radioactive sources in the industry may be replaced by the solid radioactive source prepared by the present disclosure.

The present disclosure also provides a radioactive source, including a moulding material, and a radiopharmaceutical whose half-life is shorter than a preset threshold, where the radiopharmaceutical is evenly dispersed in the moulding material. The moulding material includes a curing agent or a water-absorbing material. The curing agent includes gelatin or gypsum powder. The water-absorbing material includes a hydrogel.

For simplicity and illustrative purposes, the present disclosure is described by referring mainly to examples thereof. In the above descriptions, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

The above description is merely preferred examples of the present disclosure and is not intended to limit the present disclosure in any form. Although the present disclosure is disclosed by the above examples, the examples are not intended to limit the present disclosure. Those skilled in the art, without departing from the scope of the technical scheme of the present disclosure, may make a plurality of changes and modifications of the technical scheme of the present disclosure by the method and technical content disclosed above.

Therefore, without departing from the scope of the technical scheme of the present disclosure, based on technical essences of the present disclosure, any simple alterations, equal changes and modifications should fall within the protection scope of the technical scheme of the present disclosure. Accordingly, other embodiments are within the scope of the following claims.

The invention claimed is:

1. A method of preparing a radioactive source, comprising:
   preparing a preset dose of a radiopharmaceutical, wherein the radiopharmaceutical is Fludeoxyglucose F 18, and a half-life of the radiopharmaceutical is shorter than 7 days; and
   obtaining a solid radioactive source having a predetermined shape by mixing and moulding the radiopharmaceutical with a preset solution and a moulding material, the solid radioactive source is for diagnosing a Positron Emission Tomography (PET) device, wherein preset solution comprises water or sodium chloride solution
   wherein mixing and moulding the radiopharmaceutical with the preset solution and the moulding material comprises:
      mixing the radiopharmaceutical with the preset solution to obtain a second mixture;
      preparing a water-absorbing material as the moulding material, wherein the water-absorbing material comprises a hydrogel, and the hydrogel and the second mixture are mixed according to a ratio range of 1:150 to 2000;
   and to obtain the solid radioactive source.

2. The method of claim 1, wherein diagnosing the PET device comprises any of the following:
   quality inspection of the PET device;
   correction factor generation of the PET device; and
   calibration of the PET device.

* * * * *